(12) United States Patent
Rademaker

(10) Patent No.: US 11,464,859 B2
(45) Date of Patent: Oct. 11, 2022

(54) PHARMACEUTICAL COMPOSITIONS COMPRISING SODIUM META ARSENITE FOR TREATMENT OF MULTIPLE MYELOMA

(71) Applicant: KOMINOX, INC., Grand Cayman (KY)

(72) Inventor: Bernardus Rademaker, Onstwedde (NL)

(73) Assignee: KOMINOX, INC., Grand Cayman (KY)

( * ) Notice: Subject to any disclaimer, the term of this patent is extended or adjusted under 35 U.S.C. 154(b) by 0 days.

(21) Appl. No.: 15/077,373

(22) Filed: Mar. 22, 2016

(65) Prior Publication Data

US 2016/0199411 A1     Jul. 14, 2016

Related U.S. Application Data

(62) Division of application No. 11/631,962, filed as application No. PCT/KR2006/001731 on May 9, 2006.

(30) Foreign Application Priority Data

May 9, 2005   (EP) .................................... 05076071

(51) Int. Cl.
| | |
|---|---|
| *A61K 45/06* | (2006.01) |
| *A61K 33/36* | (2006.01) |
| *A61P 35/04* | (2006.01) |
| *A61P 7/00* | (2006.01) |
| *A61P 35/00* | (2006.01) |
| *A61P 35/02* | (2006.01) |

(52) U.S. Cl.
CPC .............. *A61K 45/06* (2013.01); *A61K 33/36* (2013.01); *A61P 7/00* (2018.01); *A61P 35/00* (2018.01); *A61P 35/02* (2018.01); *A61P 35/04* (2018.01)

(58) Field of Classification Search
CPC ......... A61K 33/36; A61K 45/06; A61P 13/00; A61P 13/08; A61P 15/00; A61P 19/00; A61P 19/08; A61P 29/00; A61P 35/00; A61P 35/02; A61P 35/04; A61P 7/00
See application file for complete search history.

(56) References Cited

U.S. PATENT DOCUMENTS

| | | |
|---|---|---|
| 4,166,452 A | 9/1979 | Constantine |
| 4,256,108 A | 3/1981 | Theeuwes |
| 4,265,874 A | 5/1981 | Bonsen et al. |
| 5,889,048 A | 3/1999 | Vorobieva |
| 8,945,505 B2 | 2/2015 | Yang |
| 2002/0183385 A1 | 12/2002 | Ellison et al. |
| 2003/0211171 A1 | 11/2003 | Warrell et al. |
| 2006/0104292 A1 | 5/2006 | Gupta et al. |
| 2009/0011047 A1 | 1/2009 | Rademaker |
| 2009/0246291 A1 | 10/2009 | Burger et al. |

FOREIGN PATENT DOCUMENTS

| | | |
|---|---|---|
| EP | 804928 A1 | 11/1997 |
| EP | 2762145 A1 | 8/2014 |
| KR | 1993-0001917 | 2/1993 |
| KR | 2002-0083458 A | 11/2002 |
| KR | 2002-0083678 A | 11/2002 |
| KR | 2005-0081594 A | 8/2005 |
| WO | WO 1980/000245 | 2/1980 |
| WO | 95/22336 A1 | 8/1995 |
| WO | 99/018798 A1 | 4/1999 |
| WO | WO 1999/055344 A1 | 11/1999 |
| WO | WO 2003/047524 A2 | 6/2003 |
| WO | 03/086424 A1 | 10/2003 |
| WO | WO 2006/121280 A1 | 11/2006 |
| WO | 2009/120697 A2 | 10/2009 |
| WO | 2011/031890 A2 | 3/2011 |

OTHER PUBLICATIONS

Munshi et al. 2002, Leukemia, 16, 1835-1837.*
Hershko et al., "Arsenite inhibits interleukin-6 production in human intestinal epithelial cells by down-regulating nuclear factor-kappaB activity", Clinical Science, vol. 103, No. 4, pp. 381-390 (2002).
Sakurai et al., "Evaluation of immunotoxic and immunodisruptive effects of inorganic arsenite on human monocytes/macrophages", Int. Immunopharmacol., vol. 4, No. 13, pp. 1661-1673 (2004).
U.S. Office Action issued in U.S. Appl. No. 11/631,962 dated Mar. 25, 2016.
Korean Office Action issued in Korean Application No. 10-2016-7007395, dated Apr. 25, 2016, with English Translation.
Experimental Hematology (2013), Supplements [online] [retrieved on Jun. 12, 2013], Retrieved from the Internet <URL: http://www.exphem.org/supplements>.

(Continued)

*Primary Examiner* — Kara R McMillian
(74) *Attorney, Agent, or Firm* — McDermott Will & Emery LLP

(57) ABSTRACT

The present application relates to pharmaceutical compositions and methods for treatment of urogenital diseases and bone metastasis in a human, which pharmaceutical composition contains an effective amount of arsenous acid alkaline or earth alkaline metal salt and/or a pharmaceutically acceptable adjuvant. According to the present invention, the alkaline arsenous acid metal salt is sodium meta-arsenita ($AsO_2Na$) or potassium meta-arsenite ($AsO_2K$). The effective amount of arsenous acid alkaline or earth alkaline metal salt is 0.0001-1500 mg/kg, preferably 1-1000 mg/kg, more preferably 1-150 mg/kg, and most preferably 50-100 mg/kg of body weight/day. The administration form of the pharmaceutical compositions of the invention is preferably oral, such as a tablet, capsule, powder and/or solution with a pharmaceutically acceptable carrier, diluent or excipient.

4 Claims, No Drawings

(56) References Cited

OTHER PUBLICATIONS

U.S. Office Action issued in U.S. Appl. No. 12/879,347 dated Jun. 24, 2014.
Chao, et al., "Inhibition by arsenite of anticancer drug cis-diamminedichloroplatinum(II) induced DNA repair and drug resitatnce in HeLa cells," Enviromental Toxicolgy an Pharmacology I (1996) 199-205.
Canadian Office Action issued in Canadian Application No. 2840609 dated Nov. 3, 2014.
Chinese Office Action issued in Chinese Application No. 200680025032.0 dated Nov. 6, 2014 w/English translation.
English Translation of Technical Detailed Report regarding response filed Oct. 1, 2013. (3 pages).
Indian Office Action issued in Indian patent Application No. 9174/DELNP/2007 dated Mar. 14, 2013.
Taiwanese Office Action, and English translation thereof, issued in Taiwanese Patent Application No. 095116432 dated Mar. 7, 2012.
Beer, Tomasz M., et al. "Southwest Oncology Group Phase II Study of Arsenic Trioxide in Patients with Refractory Germ Cell Malignancies." Interdisciplinary International Journal of the American Cancer Society. Online publication May 10, 2006. pp 2624-2629, vol. 106 / No. 12.
Vuky, Jacqueline et al., "Phase II Trial of Arsenic Trioxide in Patients with Metastatic Renal Cell Carcinoma." The Journal of New Anticancer Agents, pp. 327-330, Aug. 2002, vol. 20 / No. 3.
Soignet, Steven L. et al., "Clinical Study of an Organic Arsenical, Melarsoprol, in Patients with Advanced Leukemia." Cancer Chemotherapy and Pharmacology, pp. 417-421, Nov. 1999, vol. 44 / No. 5.
Rousselot, P. et al., "A Clinical and Pharmacological Study of Aresenic Trioxide in Advanced Multiple Myeloma Patients." Leukemia, pp. 1518-1521, Published online Jul. 22, 2004.
Litzow, Mark R. et al., "A Phase II Trial of Arsenic Trioxide for Relapsed and Refractory Acute Lymphoblastic Leukemia." Haematologica: the Hematology Journal, pp. 1105-1108, Aug. 8, 2006, vol. 91 / No. 8.
Gallagher, A. et al., "Arsenic Trioxide (ATO) in Metastatic Hormone-Refractory Prostate Cancer (HRPC): Results of Phase II trial T99-0077." Journal of Clinical Oncology, p. 4638, Jul. 15, 2004, vol. 22 / No. 14S.
Kim, Kevin B. et al., "A Phase II Trial of Arsenic Trioxide in Patients with Metastatic Melanoma." American Cancer Society, pp. 1687-1692. Published online Aug. 29, 2005, vol. 104 / Issue 8.
F. I. Abdullaev, et al.: "Cytotoxic effect of three arsenic compounds in HeLa human tumor and bacterial cells", ELSEVIER, Genetic Toxicology and Environmental Mutagenesis, Mutuation Research 493, 2001, pp. 31-38.
Office Action issued by the Egyptian Patent Office dated Jul. 2, 2013 in an unrelated patent family owned by the same assignee.
Chinese Office Action, and English translation thereof, issued in Chinese Patent Application No. 200680025032.0 dated Jul. 10, 2012.
European Office Action issued in European Patent Application No. 11165670.8 dated Oct. 9, 2012.
Chinese Office Action, with English Translation, issued in Chinese Patent Application No. 200680025032.0, dated Dec. 28, 2011.
Israeli Office Action, with English translation, issued in Israel Patent Application No. 187220, dated Feb. 7, 2012.
English translation of Egyptian Office Action issued in Egyptian Patent Application No. PCT/NA 2004/000106 dated Oct. 10, 2004.
Abdullaev, Fikrat I. et al. "Cytotoxic effect of three arsenic compounds in HeLa human tumor and bacterial cells." Genetic Toxicology and Environmental Mutagenesis, pp. 31-38. Feb. 21, 2001.
Korean Office Action issued in Korean Application No. 10-2007-7028751 dated Sep. 27, 2013, with English translation, 6 pgs.
Taiwanese Office Action issued in Application No. 101132058 dated Apr. 15, 2015, with Full English Translation.
Lee et al. KR-20020083458 Machine English translation provided.
English translation of First Chinese Office Action issued in Chinese Patent Application No. CN 200680025032.0 dated Feb. 26, 2010.
Second Chinese Office Action, w/ English translation thereof, issued in Chinese Patent Application No. 200680025032.0 dated May 18, 2011.
Kim, H., et al., "Intracellular Glutathione Level Modulates the Induction of Apoptosis by D12—Prostaglandin J2", Prostaglandins, 1996, pp. 413-425, vol. 51, Elsevier Science Inc, USA.
Zips, D., et al., "New Anticancer Agents: In Vitro and In Vivo Evaluation", in vivo, 2005, pp. 1-8, vol. 19.
Soucy, N.V., et al., "Arsenic Stimulates Angiogenesis and Tumorigenesis In Vivo", Toxicological Sciences, 2003, pp. 271-279, vol. 76, Society of Toxicology.
The Merck Index, An Encyclopedia of Chemicals, Drugsand Biologicals, Eleventh Edition, 1989, p. 1356, Merck & Co., Inc, USA.
Blakley., B.R., "The Effect of Arsenic on Urethan-induced Adenoma Formation in Swiss Mice", Can J Vet Res, 1987, pp. 240-243, vol. 51.
Huang, R.Y., et al., "Posttreatment with sodium arsenite is coclastogenic in log phase but not in stationary phase", Human Genetics, 1987, pp. 159-162, vol. 75.
Repetto, Guillermo et al., "Comparative in vitro effects of sodium arsenite and sodium arsenate on neuroblastoma cells," Toxicology 92 (1994), pp. 143-153, vol. 92, 1994 Elsevier Science Ireland Ltd., XP-002352922.
Waxman, Samuel et al., "History of the Development of Arsenic Derivatives in Cander Therapy," The Oncologist 2001; 6 (suppl 2), pp. 3-10, XP-001087583.
Chou, Ruey-Hwang et al., "Restoration of p53 tumor suppressor pathway in human cervical carcinoma cells by sodium arsenite," Biochemical and Biophysical Research Communications (2002), pp. 298-306, vol. 293, 2002 Elsevier Science (USA), XP-002352923.
European Search Report and Written Opinion issued in European Patent Application No. EP 06732912.8-2123 dated Jan. 19, 2009.
Kim et al. "Involvement of p38 Mitogen-Activated protein Kinase in the Cell Growth Inhibition by Sodium Arsenite" Journal of Cellular physiology 190, pp. 29-37 Wiley Liss, Inc 2002.
Hernandez-Zavala et al. "Effects of Arsenite on Cell Cycle Progression in Human Bladder Cancer Cell Line" Toxicology vol. 207 pp. 49-57 Elsevier 2005 www.elsevier.com/locate/toxicol.
European Search Report issued in European Patent Application No. 06732912.8-2123, dated May 15, 2009.
Russian Office Action, with English translation, issued in Russian Patent Application No. 2007145489/14(049842), dated Dec. 8, 2009.
M.J. Mccabe, Jr. et al., "Sensitivity of Myelomonocytic Leukemia Cells to Arsenite-Induced Cell Cycle Disruption, Apoptosis, and Enhanced Differentiation Is Dependent on the Inter-Relationship between Arsenic Concentration, Duration of Treatment, and Cell cycle Phase," The Journal of Pharmacology and Experimental Therapeutics, vol. 295, No. 2, 2000.
D.E. Muscarella et al., "Differential Activation of the c-Jun N-Terminal Kinase Pathway in Arsenite-Induced Apoptosis and Sensitization of Chemically Resistant Compared to Susceptivle B-Lymphoma Cell Lines," Toxicological Sciences 68, pp. 82-92 (2002).
European Search Report issued in European Patent Application No. EP 11165670.8 dated Jul. 29, 2011.
English translation of Singapore Office Action issued in Singapore Patent Application No. 200717614-2 dated Jun. 9, 2011.
Attached narrative regarding Korean court judgment and the Seoul central District Court decision (May 20, 2010).

\* cited by examiner

PHARMACEUTICAL COMPOSITIONS COMPRISING SODIUM META ARSENITE FOR TREATMENT OF MULTIPLE MYELOMA

RELATED APPLICATIONS

This application division of U.S. application Ser. No. 11/631,962, filed on Sep. 4, 2008, which is the U.S. National Phase under 35 U.S.C. § 371 of International Application No. PCT/KR2006/001731 filed on May 9, 2006, which in turn claims the benefit of European Patent Application No. 05076071.9, filed on May 9, 2005, the disclosures of which applications are incorporated by reference herein.

1. INTRODUCTION

Cancer is a significant health problem in the world. Although advances have been made in cancer detection and treatment, no vaccine or other universally successful preventive or therapeutic method is currently available. Management of the disease currently relies on a combination of early diagnosis and aggressive treatment, which may include one or more of a variety of therapies such as surgery, radiotherapy, chemotherapy and hormone therapy. While such therapies provide benefit to many patients, a high mortality continues to be observed for many cancers. The development of improved anti-tumour agents would facilitate cancer prevention and treatment.

Unfortunately, cancer is the leading cause of death, second only to heart disease, of both men and women. In the fight against cancer, numerous techniques have been developed and are the subject of current research directed to understanding the nature and cause of the disease and to providing methods for the control or cure thereof.

Although thousands of potential anti-cancer agents have been evaluated, the treatment of human cancer remains fraught with complications, which often present an array of suboptimal treatment choices. As such, chemotherapeutic agents, which possess little or no toxicity, which are inexpensive to obtain or manufacture, which are well tolerated by the patient, and which are easily administered would be a desirable addition to the therapeutic modalities currently available to the oncologist. Agents that will selectively sensitise malignant tissue to allow lower doses of radiation or therapy to achieve the same therapeutic effect with less damage to healthy tissues are also desirable. Similarly, agents that prevent cancer from occurring or reoccurring are also desirable. The present invention remedies these needs by providing such chemotherapeutic and sensitising agents.

Therefore, the technical problem underlying the present invention is to provide alternative or further compounds with anti-cancer activity and methods for the clinical use.

This problem is solved by the provision of the embodiments as defined in the claims.

The compounds of this invention are useful in treating cancer. They are effective in inhibiting survival and/or growth of cancer cells and/or for inhibiting undesirable cell growth in general.

This invention further provides pharmaceutical and therapeutic compositions which contain a pharmaceutically or therapeutically effective amount of these compounds and therapeutic methods and methods of treatment employing such compounds. In particular, this invention relates to methods of treating cancer by administration of the oral arsenous acid sodium salt disclosed herein.

The role of arsenic trioxide in the treatment of cancer as described by several inventors is different from this invention, whereas the role of arsenic (WO 800245; Komipharm International) for the treatment of malignancies was limited to primary tumours.

Also claimed is a kit for inhibiting abnormal cell growth comprising of arsenous acid sodium salt and/or synthetic analogues, modifications and pharmacologically active fragments thereof.

Before the present compounds, compositions, formulations, and methods are described, it is to be understood that this invention is not limited to the particular compounds methods, compositions, and therapeutic indications described herein, as such methods, compositions, and therapeutic indications, of course, vary. It is also to be understood that the terminology used herein is for the purpose of describing particular embodiments only, and is not intended to limit the scope of the present invention, which is only defined by the appended claims.

As used herein, including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" includes reference to equivalent steps and methods known to a person of ordinary skill in the art, and so forth.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patent, and other references discussed above are provided solely for their disclosure prior to the filing date of the present application. Nothing herein is to be construed as an admission that the invention is not entitled to antedate such disclosure by virtue of its prior invention. All publications, patent applications, patent, and other references mentioned herein are incorporated by reference in their entirety including all figures and drawings.

Prior to setting forth the invention it may be helpful to an understanding thereof to set forth definitions of 25 certain terms to be used hereinafter.

A "patient" for the purposes of the present invention includes humans and other animals, particularly mammals, and other organisms. Thus the methods are applicable to both human therapy and veterinary applications. In the preferred embodiment the patient is a mammal, and in the most preferred embodiment the patient is human.

The term "animal" refers to an organism with a closed circulatory system of blood vessels and includes birds, mammals and crocodiles. The term "animal" used here also includes human subjects.

The term "angiogenesis" refers to the generation of new blood vessels into cells, tissue, organs or tumours.

The term "metastasis" refers to the process by which tumour cells are spread to distant parts of the body. The term is also used herein to refer to a tumour that develops through the metastatic process.

The term "contacting" is used herein interchangeably with the following: combined with, added to, mixed with, passed over, incubated with, flowed over, etc. Moreover, the compounds of present invention can be "administered" by any conventional method such as, for example, parenteral, oral, and topical and inhalation routes as described herein.

As used herein, the term "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. What is meant by a "therapeutically effective amount" is an amount of a compound of the present invention effective to yield the desired therapeutic response. This amount for example could be effective in delaying the growth, delaying metastasis inhibiting angiogenesis and/or telomere and/or causing shrinkage of cancer, either a sarcoma or lymphoma. The specific safe and effective amount or therapeutically effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

"An anti-angiogenic" amount refer to an amount of a compound or composition effective to depress, suppress or inhibit angiogenesis or result in amelioration of symptoms associated with an angiogenic disease. The desired result can be either a subjective relief of a symptom(s) or an objectively identifiable improvement in the recipient of the dosage, a decrease in the vascularisation of endothelial cells or a decrease in the rate of angiogenesis as noted by a clinician or other qualified observer.

The terms "treating cancer," "therapy," and the like refer generally to any improvement in the mammal having the cancer wherein the improvement can be ascribed to treatment with the compounds of the present invention. The improvement can be either subjective or objective. For example, if the mammal is human, the patient may note improved vigour or vitality or decreased pain as subjective symptoms of improvement or response to therapy. Alternatively, the clinician may notice decrease in tumour size or tumour burden based on physical exam, laboratory parameters, tumour markers or radiographic findings. Some laboratory signs that the clinician may observe for response to therapy include normalization of tests such as white blood cell count, red blood cell count, platelet count, erythrocyte sedimentation rate, and various enzyme levels. Additionally, the clinician may observe a decrease in a detectable tumour marker. Alternatively, other tests can be used to evaluate objective improvement such as sonograms, nuclear magnetic resonance testing and positron emissions testing.

"Inhibiting the growth of tumour cells" can be evaluated by any accepted method of measuring whether growth of the tumour cells has been slowed or diminished. This includes direct observation and indirect evaluation such as subjective symptoms or objective signs as discussed above.

Accordingly, the compositions of the invention are administered to cells. By "administered" herein is meant administration of a therapeutically effective dose of the candidate agents of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant almost any cell in which mitosis or meiosis can be altered.

Therefore, the present invention related to a pharmaceutical anti-cancer composition comprising a therapeutically effective amount of arsenous acid sodium salt represented by the following formula (I):

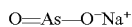

2. FIELD OF INVENTION

The present invention relates to compounds, methods and compositions for the treatment of primary and metastatic neoplastic diseases, including, but not limited to urogenital carcinomas.

More specifically, the present invention relates to novel chemotherapeutic compositions of arsenous acid sodium salt methods—novel uses of oral arsenic compounds for treating prostate cancer, primary and metastatic tumours of the urogenital system; and bladder, kidney, testicular and metastatic bone cancer.

3. BACKGROUND TO THE INVENTION

The majority of chemotherapeutic drugs are currently developed for intravenous use. Oral treatment with anti-cancer agents, however, is now of interest due to the benefits of easy administration, better patient compliance and the reduction in cost and the increase in the quality of life of the patients. For example, patients will be able to undergo oral treatment as outpatients.

Therefore, it is clear that oral drugs for cancer treatment have a future and will play a more important role than they have done in the past. Patient's preferences and quality of life issues, which are becoming central considerations in palliative treatment regimens, precede the development of orally administered drugs. Intravenous (iv) administration is a major source of discomfort and stress for cancer patients and approximately 90% of patients asked, express a preference for oral versus iv chemotherapy, predominantly because of the convenience of administration outside a clinical setting or current concerns about previous problems with intravenous access.

One of the key objectives of the present invention to provide a chemotherapeutic product for the treatment of cancer and which exhibits high bioavailability, enhanced anti-cancer activity and high level of safety following oral administration.

3.1 Urogenital Cancer

Genitourinary malignancies are composed of (amongst others) cancers of the prostate, bladder, kidney, and testis. The challenges presented by these malignancies parallel those confronting investigators and practicing clinicians in treating all other types of cancers. Smoking, which is strongly associated with the development of lung cancer, is responsible for one third of bladder cancers, and several studies implicate obesity with an increased risk for colon, breast, and kidney cancers.

3.2 Bladder Cancer

Carcinomas of the urinary tract occur in 90% of the cases directly in the bladder, 8% in the renal pelvis and 2% in the ureter or urethra. Bladder cancer is the fourth most common cancer in men and the eighth in women. Estimates are that 25% of the bladder cancers in men are related to occupational exposure and 50% to cigarette smoking. Smoking is a key determining risk, which persists for up to 10 years after smoking cessation. The choice of treatment is based on disease extent: superficial, invasive or metastatic. Combination chemotherapy is used to treat metastatic disease. Urothelial tumours are chemosensitive, and a number of single agents result in short-term regressions in 20 to 30 percent of cases. One regimen is called the MVAC regimen. It consists of combination treatment with methotrexate, vinblastine, adriamycin (doxorubicin) and cisplatin. Several drugs are given over a few days with the drugs then being repeated every few weeks for several months.

3.3 Renal Cancer

Renal cell carcinoma accounts for 90 to 95 percent of malignant neoplasm's arising from the kidney. Renal cell carcinoma affects more than 30,000 American annually and is responsible for nearly 12,000 deaths in the United States each year. Renal cell carcinoma occurs most commonly in adults between 50 and 70 years of age, although it has been reported in children as young as 3 years. Renal carcinoma is responsible for approximately 3% of adult malignancies, and the male to female ratio is 1.5:1. A strong correlation exists between cigarette smoking and the development of renal cell carcinoma. Unproven factors that may increase the risk for renal cell carcinoma include polycystic kidney disease, diabetes mellitus, and chronic dialysis. Up to 85% of renal cell carcinomas are of the clear cell type; 5% to 15% of renal cell carcinomas are a papillary histologic variant. The main type of treatment for cancer of the kidney is surgery although radiotherapy may also be recommended. In some people, hormonal treatment or biological treatment can be used either after surgery or when a cancer cannot be removed surgically. Very occasionally, cancer of the kidney will spontaneously improve without any treatment, but this is rare. Chemotherapy has not yet been shown to be helpful in treating cancer of the kidney.

3.4 Testicular Cancer

Testicular cancer primarily affects young men in the 20 to 44 year old age group, where it is the most common cancer. Overall, testicular cancer is not very common. Testicular cancer responds particularly well to treatment, and over 9 in 10 patients are cured. Primary germ cell tumours (GCTs) of the testis, arising by the malignant transformation of primordial germ cells, constitute 95 percent testicular neoplasms. This disease is notable for the young age of the afflicted patients, the totipotent capacity for differentiation of the tumour cells and its curability; more than 90 percent of all newly diagnosed patients will be cured, and, since the advent of cisplatin-based chemotherapy about 70 to 80 percent of patients with metastatic disease are cured.

Surgery, radiotherapy and chemotherapy are the commonly used treatments, depending on the stage of the cancer and whether is has spread. Chemotherapy is more often used for non-seminoma testicular cancers, however it is also used for seminoma, which has spread. Testicular cancer can be treated with different combinations of drugs with the combination most often used being BEP, Bleomycin, Etoposide and Cisplatin.

3.5 Prostate Cancer

Cancer of the prostate is the most common malignancy in men in the United States and the third most common cause of cancer death in men above the age of 55 (after carcinomas of the lung and colon). Surgery is the most common treatment for early-stage prostate cancer with radiation therapy being the second. There are also different forms of hormonal therapy. Prostate cancer cells do not tend to grow rapidly like some other types of cancer. For this reason traditional chemotherapy drugs have not proven to be quite as useful as they have been in some of the other major cancers. Nonetheless, some standard chemotherapies have been shown to be useful—particularly in late-stage prostate cancer. Although there are three chemotherapy drugs approved by the U.S. Food and Drug Administration for use in prostate cancer—Taxotere® (docetaxel), Novantrone® (mitoxantrone hydrochloride) and Emcyt® (estramustine sodium phosphate)—a number of the most common chemotherapeutics approved for other cancers are used on an "off-label" basis for late-stage prostate cancer. Chemotherapy is typically utilized in patients with advanced stage prostate cancer who are no longer responding to hormonal therapy. None of these agents are consistently helpful in the disease. The most common sites of metastases in patients with prostate cancer are the bone and lymph nodes. The bone metastases are particularly troublesome in that they can create intense pain for the patient.

3.6 Secondary Bone Cancer

Secondary bone cancer does not start in the bone, but is the result of cancer cells spreading to the bone from the primary tumour. Sometimes only one area of bone is affected, but in other people a number of bone secondaries develop, often in different bones in the body. Although any type of cancer can spread to the bone, the most common types are cancers of the breast, prostate, lung, kidney and thyroid. The treatment for a secondary bone cancer depends on the type of primary cancer. For example, prostate cancer cells may have broken away from the prostate gland, traveled in the blood to the bone and begun to grow and multiply there. So the cancer cells in the bone will respond to the same type of treatment as the cancer cells in the prostate. Although a secondary bone cancer can occur in any bone in the body, the most commonly affected bones are those of the spine, ribs, pelvis, skull and the upper bones of the arms and legs.

3.7 Arsenic and its Medical Uses

Arsenic has been used as a pharmaceutical agent for more than 2400 years to treat a large variety of diseases including cancer, but it is also a poison and carcinogenic agent. With the rapid evolvement of medicine in the 20th century, the use of medicinal arsenic waned rapidly. Interest in arsenic compounds revived when it was shown that daily intravenous administration of arsenic trioxide alone caused complete responses in a large majority of patients with newly diagnosed and relapsed acute promyelocytic leukaemia. Additional trials are underway in patients with haematological malignancies and solid tumours such as prostate and pancreatic cancer. A drawback of arsenic trioxide is that it is administered intravenously daily in 1-4-hr infusion for up to 6 weeks. A pilot study with an oral formulation of arsenic trioxide in patients with acute promyelocytic leukaemia is ongoing. The preliminary results show that the efficacy and side effects are comparable with intravenous arsenic trioxide. The same was noted for a pilot study with oral tetraarsenic tetrasulphide given to patients with acute promyelocytic leukaemia. Thus, an oral arsenic agent with similar or better efficacy in leukaemia and solid tumours and fewer side effects, particularly in patients in whom long term treatment is required, would have costs and quality-of-life benefits.

Arsenic exists in both trivalent and pentavalent oxidation states as a chemically unstable sulphide or oxide, or as a salt of sodium, potassium or calcium. Trivalent arsenicals comprising sodium arsenite and arsenic trioxide inhibit many enzymes by reacting with biological ligands that possess available sulphur groups. Pentavalent arsenic is an uncoupler of mitochondrial oxidative phosphorylation. It is thus not surprising that arsenic trioxide exerts anti-tumour effects by activating apoptosis, induction of reactive oxygen species, inhibition of angiogenesis and in acute promyelocytic leukaemia cells also by degradation of PML-RAR∝ fusion protein. The response depends upon cell type and the form of arsenic.

In 1991 the National Cancer Institute reported that arsenic trioxide inhibits growth and promotes apoptosis in many different cancer cell lines and began a research programme to evaluate its clinical activity in haematologic malignancies, such as acute promyelocytic leukaemia, acute myeloid leukaemia, acute lymphocytic leukaemia, chronic myelogenous leukaemia, non-Hodgkin's lymphoma, Hodgkin's disease, chronic lymphocytic leukaemia, myelodysplastic syndrome, and multiple myeloma. It is also supporting research in solid tumours, such as advanced hormone-refractory prostate cancer and renal cell cancer and in cervical cancer and refractory transitional cell carcinoma of the bladder.

Other clinical studies are underway, including Phase II Studies in Solid Tumours. Based on promising pre-clinical data, NCI-sponsored clinical trials to examine the potential of arsenic trioxide for the treatment of solid tumours are under way or in the final planning stages.

4. SUMMARY OF THE INVENTION

The present invention relates to a pharmaceutical composition intended for the treatment of urogenital diseases and bone metastasis and to a method of treating such diseases.

Accordingly, the present invention provides a pharmaceutical composition intended for the treatment of urogenital diseases and bone metastasis in a human, wherein said pharmaceutical composition contains an effective amount of arsenous acid alkaline or earth alkaline metal salt and/or a pharmaceutically acceptable adjuvant.

According to the present invention, said alkaline arsenous acid metal salt is sodium meta-arsenite ($AsO_2Na$) or potassium meta-arsenite ($AsO_2K$).

The effective amount of arsenous acid alkaline or earth alkaline metal salt is 0.0001-1500 mg/kg, preferably 1-1000 mg/kg, more preferably 1-150 mg/kg, and most preferably 50-100 mg/kg of body weight/day.

Said pharmaceutical composition preferably occurs in an oral administration form, wherein said oral administration form is e.g. a tablet, capsule, powder and/or solution with a pharmaceutically acceptable carrier, diluent or excipient.

Said urogenital disease comprises essentially cancer of the prostate, bladder, kidney and testis.

According to the invention, a chemotherapeutic product comprises of arsenous acid sodium salt having the formula (I):

$O=As-O^-Na^+$

Furthermore, the invention includes pharmaceutical compositions comprising such products together with a pharmaceutically acceptable carrier or diluent. Suitable carriers and diluents are well known, as are the principles of formulation of compositions in unit dosage form and for oral administration.

In a further aspect, the invention includes a method for the treatment of cancer in an animal or human body, the method comprising the simultaneous, separate or sequential administration to the said body of arsenous acid sodium salt.

The Inventor has explored the potency of three arsenic compounds of different valence and methylation in panels of human tumour cell lines in vitro, arsenous acid sodium salt ($As^{3+}$), dimethylarsinic acid ($As^{5+}$) and arsenic acid ($As^{5+}$).

Surprisingly arsenous acid sodium salt was the most potent and showed anti-tumour activity in a human tumour model in vivo, reason to develop arsenous acid sodium salt further as a novel arsenic compound. Arsenous acid sodium salt surprisingly was more potent in vitro and showed differential activity in leukaemia, melanoma and mammary cancer lines than $As_2O_3$. Arsenous acid sodium salt is surprisingly capable of shortening telomeres of human cancer cells, inducing cellular senescence and chromosomal abnormalities, but does not directly inhibit the telomerase activity. The effects indicate that arsenous acid sodium salt is a telomere inhibitor. Arsenous acid sodium salt was rapidly absorbed after both i.v. and p.o. administration and remained in the plasma for prolonged periods. Surprisingly the bioavailability of oral arsenous acid sodium salt was approximately 100%. Animal toxicity studies showed that the main target organs were bone marrow and lymphoid organs. Thus arsenous acid sodium salt can be administered orally. It might be used in long-term treatment of cancer patients with solid tumours or leukaemia at dose levels below the maximum tolerated dose (MTD), alone or in combination with another treatment modality, maintaining a good quality of life.

This compound ($NaAsO_2$) of the present invention has been developed as novel anti-cancer agent. The compound possesses good cytotoxic activity in a panel of 43 human tumour cell lines in vitro with an IC50 value of 0.6 μM. Pronounced selectivity was observed in tumour cell lines derived from leukaemia, mammary cancer and melanoma. In a head-to-head comparison arsenous acid sodium salt was surprisingly at least 15-fold more potent than the clinically used agent arsenic trioxide and had also a better differential activity. Arsenous acid sodium salt combined with 5-fluoruracil (5-FU) or vinblastine may result in additive effects. Potassium in the arsenite reduced cytotoxic activity.

In vivo arsenous acid sodium salt (oral and intraperitoneal) was surprisingly borderline active in ⅔ subcutaneously transplanted human tumour xenografts (renal cell carcinoma RXF 944LX and mammary cancer MAXF 401). In general the highest efficacy of arsenous acid sodium salt was obtained with doses of ⅓-⅔ of the maximum tolerated dose (MTD). The efficacy of the compound was better using daily administrations of 5 or more days compared with intermittent schedules (every 4 days×3, weekly×3).

Surprisingly, oral arsenous acid sodium salt showed a high therapeutic efficacy in cancer patients suffering from urogenital cancer, mainly prostate and bone metastasis, following treatment with 2.5, 10, 12.5, 15, 17.5 and 20 mg of arsenous acid sodium salt capsules for 14 consecutive days.

Surprisingly the patients all tolerated the arsenous acid sodium salt extremely well with no adverse events (AE's) or serious adverse events (SAE's) occurring. The study medication did not cause any disturbance of any patients' well-being feeling. There was no change during the course of the study in any patients' ECG activity, audiometry or neurological examinations.

Surprisingly arsenous acid sodium salt, the compound of invention, has great therapeutic and safety advantages in comparison to arsenic trioxide. Arsenic trioxide $As_2O_3$ has been shown to prolong the QT and QT interval corrected for rate ($QT_c$), which may predispose the patient to potentially fatal aytipical ventricular tachycardia and produce complete atrioventricular block.

Further more, adverse events occurring in 10% or more of patients treated with arsenic trioxide include fatigue, fever, oedema, chest pain, rigors, reactions at the injection site (ie pain, erythema, oedema), weakness, weight gain, nausea, anorexia, decreased appetite, diarrhea or loose stools, vomiting, abdominal pain, dyspepsia, sore throat, constipation, hypokalemia, hypomagnesemia, increases in serum AST (SGOT) and/or ALT (SGPT), hyperkalemia, hypocalcemia, headache, insomnia, paresthesia, dizziness, tremor, cough, dyspnea, epistaxis, hypoxia, pleural effusion, postnasal drip, wheezing, decreased breath sounds, crepitations, rales, dermatitis, pruritus, ecchymosis, dry skin, erythema, sweating, tachycardia, ECG abnormalities, sinusitis, herpes simplex, upper respiratory infection, arthralgia, myalgia, bone pain, back pain, neck pain, limb pain, leukocytosis, anaemia, thrombocytopenia, neutopenia (may be febrile), hypotension, hypertension, flushing, pallor, anxiety, depression, ocular irritation, blurred vision and vaginal haemorrhage.

Surprisingly none of these adverse events have been observed using the oral arsenous acid sodium salt, which is the compound of the present invention.

5. DETAILED DESCRIPTION OF THE INVENTION

Methods and compositions for the treatment of primary and metastatic urological neoplasm and/or bone metastasis are described herein.

The invention is based, in part, on a dosage regime for the oral administration of a composition comprising of arsenous acid sodium salt. It is also based in part, on the therapeutic efficacy of the arsenous acid sodium salt of the invention against certain cancers.

This invention includes a method of treating primary solid tumours in a mammal, which involves the administration of a non-lethal and therapeutically effective amount of arsenous acid sodium salt on its own, or in combination with one or more therapeutic agents to the mammal in need of such therapy.

The invention also includes a method for treating disorders of the blood in mammals, which involves the administration of arsenous acid sodium salt either on its own or in combination with one or more therapeutic agents into the affected mammal.

The arsenic compound of the invention, arsenous acid sodium salt, may be utilised in a variety of known forms for example as a salt, as an organic/inorganic complex, as an organic chelate or encapsulated in a drug targeting system.

It should be recognised that the invention includes arsenous acid sodium salt pro-drugs or compounds that are converted in-vivo to biologically active forms of the arsenous acid sodium salt. Such pro-drugs may be used to reduce or avoid the toxicity of the usual pharmaceutical agent or to optimise the treatment and efficacy. Arsenous acid sodium salt can be synthesised or commercially purchased.

In our embodiment, the arsenous acid sodium salt is prepared in capsules. Generally the skilled artisan will recognise that the form of arsenous acid sodium salt to be used should be therapeutically effective without unreasonable toxicity.

Any suitable route of administration of arsenous acid sodium salt may be used in accordance with the present invention including but not limited to oral administration, parenteral administration such as intravenous, subcutaneous, intramuscular and intrathecal and intranasal, rectal or vaginal administration. Administration may also be made directly into the tumour or through transdermal patches or implantation devices (particularly for slow release). Topical administration may also be used.

The pharmaceutical compositions to be used may be in the form of sterile physiologically acceptable (aqueous or organic) solutions, colloidal suspensions, creams, ointments, pastes, capsules, caplets, tablets and cachets. It should also be recognised that delayed slow or sustained release forms of administration are also included.

The arsenic compounds of the present invention may be used against a variety of primary and metastatic neoplastic diseases including, but not limited to, primary and metastatic tumours of the central nervous system, breast, colon, ovaries, kidneys, lung, liver, bladder, prostate and head and neck.

5.1 Pharmaceutical Formulation

Therefore, the present invention relates to a pharmaceutical anti-cancer composition comprising of a therapeutically effective amount of arsenous acid sodium salt represented by the following formula (I)

and its pharmaceutically acceptable salts used for the manufacturing of an agent for the treatment of a cell proliferative disorder and one or more pharmaceutically acceptable adjuvant, excipient, carrier, buffer, diluent and/or customary pharmaceutical auxiliary. In a preferred embodiment of the invention the compound of the invention can be administered in a pharmaceutically acceptable formulation. The present invention pertains to any pharmaceutically acceptable formulations, such as synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes. In addition to the compound and the pharmaceutically acceptable polymer, the pharmaceutically acceptable formulation used in the method of the invention can comprise additional pharmaceutically acceptable carriers and/or excipients. As used herein, pharmaceutically acceptable carrier includes any and all solvents, dispersion media, coatings, antibacterial and anti fungal agents, isotonic and absorption delaying agents, and the like that are physiologically compatible. For example, the carrier can be suitable for injection into the blood. Excipients include pharmaceutically acceptable stabilizers and disintegrants. In another embodiment, the pharmaceutically acceptable formulations comprise lipid-based formulations. Any of the known lipid-based drug delivery systems can be used in the practice of the invention. For instance, multi-vesicular liposomes (MVL), multi-lamellar liposomes (also known as multi-lamellar vesicles or MLV), uni-lamellar liposomes, including small uni-lamellar liposomes (also known as uni-lamellar vesicles or SUV) and large uni-lamellar liposomes (also known as large uni-lamellar vesicles or LUV), can all be used so long as a sustained release rate of the encapsulated compounds can be established. In one embodiment, the lipid-based formulation can be a multi-vesicular liposome system. The composition of the synthetic membrane vesicle is usually a combination of phospholipids, usually in combination with steroids, especially cholcompoundol. Other phospholipids or other lipids may also be used. Examples of lipids useful in synthetic membrane vesicle production include phosphatidylglycerols, phosphatidylcholines, phosphatidylserines, phosphatidylethanolaminos, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used. In another embodiment, the composition containing the compound may be incorporated or impregnated into a bio-absorbable matrix. In addition, the matrix may be comprised of the said biopolymer. A suitable biopolymer for the present invention can include also one or more macromolecules selected from the group consisting of collagen, elastin, fibronectin, vitronectin, laminin, polyglycolic acid, hyaluronic acid, chondroitin sulphate, dermatan sulphate, heparin sulphate, heparin, fibrin, cellulose, gelatin, polylysine, echinonectin, entactin, thrombospondin, uvomorulin, biglycan, decorin, and dextran. The formulation of these macromolecules into a biopolymer is well known in the art. In a preferred embodiment, the therapeutic composition is not immunogenic when administered to a human patient for therapeutic purposes.

A therapeutic composition of the present invention can include pharmaceutically acceptable salts of the components therein. Pharmaceutically acceptable salts include the acid addition salts that are formed with inorganic acids such as, for example, hydrochloric or phosphoric acids, or such organic acids as acetic, tartaric, mandelic and the like. Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes. Liquid compositions can also contain liquid phases in addition to and to the exclusion of water. Exemplary of such additional liquid phases are glycerine, vegetable oils such as cottonseed oil, organic compounds such as ethyl oleate, and water-oil emulsions. A therapeutic composition contains a polypeptide of the present invention, typically an amount of at least 0.1 weight percent of polypeptide per weight of total therapeutic composition. A weight percent is a ratio by weight of polypeptide to total composition. Thus, for example, 0.1 weight percent is 0.1 grams of polypeptide per 100 grams of total composition.

The term "pharmaceutically acceptable salt" refers to those salts of compounds which retain the biological effectiveness and properties of the free bases and which are obtained by reaction with inorganic acids such as hydrochloric acid, hydrobromic acid, sulphuric acid, nitric acid, phosphoric acid, methanesulfonic acid, ethanesulfonic acid, atoluenesulfonic acid, salicylic acid and the like.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonates sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release. A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anti-cancer drugs (e.g., TAXOL® (the trade name for the generic chemotherapy drug, paclitaxel; a chemotherapy drug which is classified as a "plant alkaloid," a "taxane" and an "antimitotic agent; Bristol Meyers Squibb, N.Y., N.Y.) or mitomycin C), anti-inflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsycotics, antipyretics, antiseptics, anti-signalling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquillisers and urinary antiinfectives.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydroxy-propylmethylcellulose, sodium alginate polyvinyl-pyrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial compounds derived from fatty acids and a hexitol such a polyoxyethylene with partial compounds derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and compounds or partial compounds derived from fatty acids and hexitol anhydrides, for example sorbitan monooleate and condensation products of the said partial compounds with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents, which have been mentioned above. The sterile injectable preparation may also be in a sterile injectable solution or suspension in a non-toxic parenterally acceptable diluent or solvent, for example as absolution in 1, 3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage levels of the order of from about 0.05 mg to about 140 mg per kilogram of body weight per: day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the abovementioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

5.1.1 Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavouring agent, such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound sucrose as a sweetening agent methyl and propylparabens as preservatives, a dye and flavouring, such as cherry or orange flavour. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerine and potassium bicarbonate, or dispersed in a dentifrice, or added in a therapeutically-effective amount to a composition that may include water, binders, abrasives, flavouring agents, foaming agents, and humectants. Alternatively the compositions may be fashioned into a tablet or solution form that may be placed under the tongue or otherwise dissolved in the mouth.

5.1.2 Injectable Delivery

In certain circumstances it will be desirable to deliver the pharmaceutical compositions disclosed herein parenterally, intravenously, intramuscularly, or even intraperitoneally. Solutions of the active compounds as freebase or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by national or regional offices of biologics standards.

Sterile injectable solutions are prepared by incorporating the active compounds in the required amount in the appropriate solvent with several of the other ingredients enumerated above, as required; followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

5.1.3 Nasal Delivery

In certain embodiments, intranasal sprays, inhalation, and/or other aerosol delivery vehicles may deliver the pharmaceutical compositions. Likewise, the delivery of drugs using intranasal microparticle resins and lysophosphatidyl-glycerol compounds are also well known in the pharmaceutical arts.

5.2 Target Cancers

The subjects treated will typically comprise of mammals and most preferably will be human subjects e.g. human cancer subjects. The compounds of the invention may be used alone or in combination. Additionally the treated compounds may be utilized with other types of treatments. For example, the subject compounds may be used with other chemotherapies e.g. tamoxifen, TAXOL®, methothrexate, biologicals such as antibodies, growth factors or lymphokines, radiation etc. Combination therapies may result in synergistic results. The preferred indication is cancer especially the cancers identified previously.

The compositions and methods provided herein are particularly deemed useful for the treatment of primary and metastatic neoplastic tumours including solid tumours such as breast, central nervous system, colon, ovarian, kidney, lung, liver, bladder, prostate, head and neck etc. More specifically, tumours, which may be treated by the compositions and methods of the invention, include tumours of an epithelial origin such as, but not limited to: Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: oesophagus (squamous cell carcinoma, adenocarcinoma), gastric carcinoma, colorectal carcinoma; Urogenital tract: kidney (adenocarcinoma, Wilm's tumour [nephroblastoma], lymphoma, leukaemia), bladder and urethra (squamous cell carcinoma, transitional cell carcinoma, adenocarcinoma), prostate (adenocarcinoma, sarcoma), testis (seminoma); Liver: hepatoma (hepatocellular carcinoma); Bone: osteogenic sarcoma (Osteosarcoma); Nervous system: neuroblastoma, Retinoblastoma, Glioblastoma, Oligodendroglioma; Gynaecological: cervix (cervical carcinoma, pre-tumour cervical dysplasia); Haematologic: blood (myeloid leukaemia [acute and chronic], acute lymphoblastic leukaemia, chronic lymphocytic leukaemia), Hodgkin's disease, non-Hodgkin's lymphoma [malignant lymphoma]; Skin: malignant melanoma, basal cell carcinoma, squamous cell carcinoma, Karposi's sarcoma and Glands and ducts: adenocarcinoma, papillary carcinoma and papillary adenocarcinoma. Thus, the term "cancerous cell" as provided herein, includes a cell afflicted by any one of the above-identified conditions.

The term "leukaemia" refers broadly to progressive, malignant diseases of the blood-forming organs and is generally characterized by a distorted proliferation and development of leukocytes and their precursors in the blood and bone marrow. Leukaemia is generally clinically classified on the basis of (1) the duration and character of the disease-acute or chronic; (2) the type of cell involved; myeloid (myelogenous), lymphoid (lymphogenous), or monocytic and (3) the increase or non-increase in the number abnormal cells in the blood-leukaemia or aleukaemic (subleukaemic). The P388 leukaemia model is widely accepted as being predictive of in vivo anti-leukaemic activity. It is believed that compound that tests positive in the P388 assay will generally exhibit some level of anti-leukaemic activity in vivo regardless of the type of leukaemia being treated. Accordingly, the present invention includes a method of treating leukaemia, and, preferably, a method of treating acute nonlymphocytic leukaemia, chronic lymphocytic leukaemia, acute granulocytic leukaemia, chronic granulocytic leukaemia, acute promyelocytic leukaemia, adult T-cell leukaemia, aleukaemic leukaemia, a leukocythemic leukaemia, basophylic leukaemia, blast cell leukaemia, bovine leukaemia, chronic myelocytic leukaemia, leukaemia cutis, embryonal leukaemia, eosinophilic leukaemia, Gross' leukaemia, hairy-cell leukaemia, hemoblastic leukaemia, hemocytoblastic leukaemia, histiocytic leukaemia, stem cell leukaemia, acute monocytic leukaemia, leukopenic leukaemia, lymphatic leukaemia, lymphoblastic leukaemia, lymphocytic leukaemia, lymphogenous leukaemia, lymphoid leukaemia, lymphosarcoma cell leukaemia, mast cell leukaemia, megakaryocytic leukaemia, micromyeloblastic leukaemia, monocytic leukaemia, myeloblastic leukaemia, myelocytic leukaemia, myeloid granulocytic leukaemia, myelomonocytic leukaemia, Naegeli leukaemia, plasma cell leukaemia, plasmacytic leukaemia, promyelocytic leukaemia, Rieder cell leukaemia, Schilling's leukaemia, stem cell leukaemia, subleukaemic leukaemia, and undifferentiated cell leukaemia.

The term "sarcoma" generally refers to a tumour which is made up of a substance like the embryonic connective tissue and is generally composed of closely packed cells embedded in a fibrillar or homogeneous substance. Sarcomas which can be treated with compound of the invention and optionally a potentiator and/or chemotherapeutic agent include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumour sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumour arising from the melanocytic system of the skin and other organs. Melanomas which can be treated with said compounds and optionally a potentiator and/or another chemotherapeutic agent include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Exemplary carcinomas which can be treated with said compound and optionally a potentiator and/or a chemotherapeutic agent include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, haematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma *villosum*.

Additional cancers which can be treated with compound according to the invention include, for example, Hodgkin's Disease, Non-Hodgkin's Lymphoma, multiple mycloma, neuroblastoma, breast cancer, ovarian cancer, lung cancer, rhabdomyosarcoma, primary thrombocytosis, primary macroglobulinemia, small-cell lung tumours, primary brain tumours, stomach cancer, colon cancer, malignant pancreatic insulanoma, malignant carcinoid, unary bladder cancer, pre-malignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

In a specific embodiment, the present invention provides compositions and methods for enhancing tumour specific immunity in individuals suffering from colorectal cancer metastasised to the liver, in order to inhibit the progression of the neoplastic disease. Preferred methods of treating these neoplastic diseases comprise administering a composition of arsenic, which elicits an immune response against tumour cells.

In another specific embodiment, the present invention provides compositions and methods for enhancing specific immunity in individuals suffering from hepatocellular carcinoma in order to inhibit the progression of the neoplastic disease and ultimately irradiate all preneoplastic and neoplastic cells.

Lastly the present invention provides hsp compositions and methods for enhancing specific immunity to preneoplastic and neoplastic mammary cells in women. The present invention also provides compositions and methods for inhibiting cancer cell proliferation and metastasis. These compositions can be applied alone or in combination with each other or with biological response modifiers.

6. WORKING EXAMPLES

The following subsections describe the testing of a pharmaceutical composition comprising arsenous acid sodium salt in vivo using cancer patients. The results demonstrate that arsenous acid sodium salt administered orally is effective in the treatment of urogenital cancer.

6.1 METHODS AND MATERIALS

Cancer patients suffering from prostate and/or urogenital cancer have been treated in an ICH-GCP clinical study with oral arsenous acid sodium salt. The patients were suffering from urogenital cancer, mainly prostate cancer and bone metastasis, not amenable to any established methods of therapy and were treated with arsenous acid sodium salt over 7 different dosing levels. Arsenous acid sodium salt is thought to act as a telomere poison as it is capable of shortening the telomeres of human cancer cells, which leads to chromosomal abnormalities but doesn't inhibit telomerase activity.

Arsenous acid sodium salt was taken daily for 14 consecutive days according to the dose level treatment scheme below:

Treatment Level 1: One capsule each 2.5 mg sodium metaarsenite daily (every 24 hours) Prior to breakfast Treatment Level 2: Two capsules each 2.5 mg arsenous acid sodium salt daily 1 prior to breakfast, 1 prior to dinner Treatment Level 3: Four capsules each 2.5 mg arsenous acid sodium salt daily 1 prior to breakfast, 2 prior to lunch, 1 prior to dinner Treatment Level 4: Five capsules each 2.5 mg arsenous acid sodium salt daily 2 prior to breakfast, 2 prior to lunch, 1 prior to dinner Treatment Level 5: Six capsules each 2.5 mg arsenous acid sodium salt daily 2 prior to breakfast, 2 prior to lunch, 2 prior to dinner Patient visits were planned for the control of the compliance, toxicity and safety and were held as follows:

Visit 1: was held between day 7 and day 0 (start of treatment)

Visit 2: on the first day of treatment with sodium metaarsenite

Visit 3: on day 8 of treatment with arsenous acid sodium arsenous acid sodium salt Visit 4: on day 15 (approx. 24 hours) after the completion of 14 consecutive days of treatment with arsenous acid sodium salt Visit 5: on day 22 (approx. 7 days after the completion of 14 consecutive days of treatment with arsenous acid sodium salt Visit 6: on day 42 (approx. 28 days) after the completion of the 14 days consecutive days of treatment with arsenous acid sodium salt The following target parameters were assessed during this study: toxicity profile, efficacy, liver enzyme parameters (GOT, GPT, cx-GT, AP), kidney function, haematology functions, tumour marker evaluations (CEA and PSA) and the pharmacokinetics of arsenous acid sodium salt.

6.2 RESULTS

Below is a summary of the clinical findings for each patient involved in this study. The findings reported include the values for the tumour markers CEA (carcinoembryonal antigen) and PSA (prostate specific antigen) and results for efficacy, toxicity and safety.

Table 1 and 2 Presents the Summary of Patient Details with PSA and CEA Values:

TABLE 1

Arsenous acid sodium salt dose groups 1, 3 and 5:

| Patient initial | Age | Dose 1 (2.5 mg) | | Dose 3 (10 mg) | | Dose 5 (15 mg) | |
|---|---|---|---|---|---|---|---|
| | | Visit 1 | Visit 6 | Visit 1 | Visit 6 | Visit 1 | Visit 6 |
| K. F. | 75 | PSA: 0.29 | PSA: 0.16 | PSA: 0.16 | PSA: 0.18 | PSA: 0.17 | PSA: 0.18 |
| | | CEA: 1.13 | CEA: 1.06 | CEA: 1.06 | CEA: 0.99 | CEA: 0.92 | CEA: 1.08 |
| G. R. | 73 | PSA: 1.61 | PSA: 0.37 | PSA: 0.37 | PSA: 0.12 | PSA: 0.11 | PSA: 0.07 |
| | | CEA: 1.29 | CEA: 1.56 | CEA: 1.56 | CEA: 1.02 | CEA: 0.10 | CEA: 1.22 |
| E. S. | 73 | PSA: 0.24 | PSA: 0.11 | PSA: 0.11 | PSA: 0.08 | PSA: 0.09 | PSA: 0.09 |
| | | CEA: 1.40 | CEA: 1.28 | CEA: 1.28 | CSA: 1.17 | CEA: 1.12 | CEA: 1.13 |
| J. S. | 84 | PSA: 0.19 | PSA: 0.21 | PSA: 0.21 | PSA: 0.27 | PSA: 0.28 | PSA: 0.24 |
| | | CEA: 2.59 | CEA: 3.38 | CEA: 3.38 | CEA: 2.48 | CEA: 2.51 | CEA: 2.65 |
| D. B. | 65 | PSA: 0.45 | PSA: <0.04 | PSA: <0.04 | PSA: <0.04 | PSA: <0.04 | PSA: <0.04 |
| | | CEA: 3.45 | CEA: 4.65 | CEA: 4.65 | CEA: 4.62 | CEA: 4.68 | CEA: 5.26 |

TABLE 2

Arsenous acid sodium salt dose groups 2 and 4:

| Patient initials | Age | Dose 2 (5 mg) | | Doge 4 (12.5 mg) | |
|---|---|---|---|---|---|
| | | Visit 1 | Visit 6 | Visit 1 | Visit 6 |
| H-W. S | 59 | PSA: 725 | PSA: 6.15 | PSA: 6.15 | PSA: 3.67 |
| | | CEA: 1.79 | CEA: 1.89 | CEA: 1.89 | CEA: 2.64 |

Surprisingly, the patients all tolerated the arsenous acid sodium salt extremely well. No adverse events (AE's) or serious adverse events (SAE's) occurred. The study medication did not cause any disturbance of any patient's well-being feeling. There was no change during the course of the study in any patient's ECG activity, audiometry or neurological examinations. None of the patients had radiotherapy prior to treatment with arsenous acid sodium salt. The arsenous acid sodium salt showed a high level of efficacy.

6.2.1 Example 1

Patient K. F.

Histology:

Advanced, inoperable, solid prostate cancer with 15 infiltration of the rectal mucosal wall, Nov. 2, 2004

Stage:

Dukes C, pT 4 Gleason score 6 Therapy

Since the patient suffers from a coronary heart disease with a myocardial infarction and implantation of coronary stents, a radical prostatovesiculectomy could not be performed and a full androgen ablation with a LHRH antagonist (one profact s.c injection every 3 months) and an oral antiandrogen (androcur tablets dosage 1×1/d after lunch) was initiated. A palliative transurethral resection of the prostate (TURP) to ameliorate micturition was performed in May 2004.

This patient took part in the dose levels 1, 3 and 5 of the arsenous acid sodium salt study. The results for this patient indicate a clinically significant change in PSA levels for all 3 drug dose levels. Dose level one (2.5 mg arsenous acid sodium salt) indicated a significant decrease in PSA from 0.29 ng/ml to 0.16 ng/ml. This decrease corresponds to a reduction in tumour activity of 44.83%. Dose level three (10 mg arsenous acid sodium salt) indicate an increase of PSA from 0.16 to 0.18 ng/ml. Dose level five (12.5 mg arsenous acid sodium salt) again indicates an increase, this time from 0.17 to 0.18 ng/ml. Neither dose level 3 or 5 showed any significant change in tumour activity.

Dose level one showed a decrease in tumour size from 20×35 mm to 20×34 mm. Dose level three also showed a decrease from 20×35 to 20×34 mm while dose level five showed no change in size from 20×34 mm.

The secondary parameters (safety parameters) showed no clinically significant results at any of the dose levels. A reversible increase in liver transaminases sGPT and sGOT was observed during the intake of arsenous acid sodium salt in dose group III and V (visit 3 and 4). In visit 5 the transaminases almost returned to normal values. This increase seems to be related to the administration of the investigative drug arsenous acid sodium salt.

The Evaluation/Judgement of Clinical Response/Progression for Dose Level One was that of a Partial Response. For Both Dose Levels Three and Five, the Disease Showed Stability.

6.2.2 Example 2

Patient G. R.

Histology:

Advanced, inoperable, solid prostate cancer with an extraglandular tumour growth Stage:

Dukes C, pT 4 Gleason score 4

Therapy

As well as suffering from a prostate carcinoma, this patient also suffered from a renal cell carcinoma (since cured by radical nephrectomy) and a superficial bladder cancer (no tumour recurrence). The patient was included in the study due the continued rising of PSA levels after a complete androgen ablation with a LHRH antagonist (one profact s.c injection every 3 months) and an oral antiandrogen (casodex tablets dosage 1×1/d after lunch).

This patient took part in the dose levels 1, 3 and 5 of the arsenous acid sodium salt study. The results for this patient indicate a clinically significant change in PSA levels for all 3 arsenous acid sodium salt dose levels. Dose level one indicated a significant decrease in PSA from 1.61 ng/ml to 0.37 ng/ml. This decrease corresponds to a reduction in tumour activity of 77.1%. Dose levels three and five indicate a decrease of PSA from 0.37 to 0.12 ng/ml and 0.11 to 0.07 ng/ml respectively. Dose level three showed a reduction in tumour activity of a further 67.56%, while dose level five showed no significant change.

Dose level one showed a decrease in tumour size from 12.5×65 mm to 0.8×30 mm. Dose level three also showed a decrease in the prostate tumour from 60×25 to 50×25 mm while dose level five showed no change in size.

The secondary parameters (safety parameters) showed no clinically significant results at any of the dose levels. Pre-study elevated triglycerides and cholesterol level had been detected which were unchanged during the course of the study. Glucose levels always appeared elevated which could be explained by alimentary reasons since blood probes were always taken in the morning after an opulent breakfast.

The Evaluation/Judgement of Clinical Response/Progression for all Three Dose Levels was that of a Partial Response.

6.2.3 Example 3

Patient E. S.

Histology:
Advanced, inoperable, solid, androgen resistant prostate cancer with an extra-capsular tumour growth.
Stage:
Dukes C, pT 4 Gleason score 4
Therapy As well as suffering from a prostate carcinoma, this patient also suffers from rectum cancer. This patient was included because of the advanced and inoperable situation. An androgen ablation with a LHRH antagonist (one profact s.c injection every 3 months) has been performed.

This patient took part in the dose levels 1, 3 and 5 of the arsenous acid sodium salt study. The results for this patient indicate a clinically significant change in PSA levels for all 3 drug dose levels. Dose levels one and three indicate a decrease of PSA from 0.24 ng/ml to 0.11 ng/ml and 0.11 to 0.08 ng/ml respectively. Dose level five showed no change from 0.09 ng/ml. Dose level one showed a reduction in tumour activity of 54.12% and level three, a further 67.56%. Dose level five showed no significant change.

Dose level one showed a decrease in tumour size from 30×35 mm to 30×30 mm. Dose levels three and five showed no change in size.

The secondary parameters (safety parameters) showed no clinically significant results at any of the dose levels. A reversible and slight increase in sGPT was detected.

The evaluation/judgement of clinical response/progression for dose levels one and three was that of a partial response. Dose level five showed disease stability.

6.2.4 Example 4

Patient J. S.

Histology:
Advanced, inoperable, androgen-resistant solid prostate cancer with an extraglandular tumour growth.
Stage:
Dukes C, pT 4 Gleason score 8
Therapy The patient was included in the study due the continued rising of PSA levels after subcapsular orchiectomy for androgen ablation.

This patient took part in the dose levels 1, 3 and 5 of the arsenous acid sodium salt study. The results for this patient indicate a clinically significant change in PSA levels for all 3 drug dose levels. Dose level one indicated an increase in PSA from 0.19 ng/ml to 0.21 ng/ml. Dose levels three and five indicate an increase of PSA from 0.21 ng/ml to 0.27 ng/ml and a decrease of PSA from 0.27 to 0.24 ng/ml respectively. Dose levels one and three showed an increase in tumour progression while dose level five showed no significant change.

Dose level one showed an increase in tumour size from 30×30 mm to 35×35 mm. Dose levels three and five showed no change from 30×35 mm.

The secondary parameters (safety parameters) showed no clinically significant results at any of the dose levels. A pre-study existing elevation of sGGT and thrombocytosis remained unchanged during the course of the study.

The Evaluation/Judgement of Clinical Response/Progression for Dose Levels One and Three was that of Progression of Disease. Dose Level Five Showed a Partial Response to the Arsenous Acid Sodium Salt.

6.2.5 Example 5

Patient D. B.

Histology:
Local recurrence of a solid prostate cancer after radical prostatectomy (stage pT2C Gleason 6) with bladder neck infiltration, inoperable.
Stage:
Dukes C, pT 4 Gleason score 6
Therapy This patient was included in the study due the continued rising of PSA levels after radical prostatectomy and complete androgen ablation with a LHRH antagonist (one profact s.c injection every 3 months) and an oral antiandrogen (casodex tablets dosage 1×1/d after lunch).

This patient took part in the dose levels 1, 3 and 5 of the arsenous acid sodium salt study. The results for this patient indicate a clinically significant change in PSA levels for drug dose levels one. Dose level one indicated a significant decrease in PSA from 0.45 ng/ml to 0.04 ng/ml. This decrease corresponds to a reduction in tumour activity of 91.11%. Dose levels three and five showed no change from 0.04 ng/ml.

The measurement of tumour lesions was not obtainable by any of the standard measuring means.

The secondary parameters (safety parameters) showed no clinically significant results at any of the dose levels. A reversible increase of liver transaminases sGOT, sGPT and sGGT was observed.

The Evaluation/Judgement of Clinical Response/Progression for Dose Level One was that of a Partial Response. For Both Dose Levels Three and Five, the Disease Showed a Complete Response to the Arsenous Acid Sodium Salt.

6.2.6 Example 6

Patient H-W. S.

Histology:
Advanced, inoperable, solid prostate cancer with an extraglandular tumour growth in the bladder neck and pelvic wall and a dissemination of bone metastases.
Stage:
Dukes C, pT 4 Gleason score 9 M2
Therapy The patient was-included in the study because of the advanced status of the detected prostate cancer with multiple bone-metastases invading the whole skeleton. A complete androgen ablation with a LHRH antagonist (one profact s.c injection every 3 months) and an oral antiandrogen (casodex tablets dosage 1×1/d after lunch) was performed.

This patient took part in the dose levels 2 and 4 of the arsenous acid sodium salt study. The results for this patient indicate a clinically significant change in PSA levels for both drug dose levels. Dose level two indicated a decrease in PSA from 725 ng/ml to 6.15 ng/ml with a decrease in tumour activity of 99.15%, while dose level four indicated a decrease of PSA from 6.15 ng/ml to 3.67 ng/ml with a further tumour activity reduction of 40.32%.

Dose level two showed a decrease in tumour size from 65×40 mm to 15×30 mm while dose level four showed no change in size from 15×40 mm.

The secondary parameters (safety parameters) showed no clinically significant results at any of the dose levels. The patients' quality of life was strongly ameliorated by arsenous acid sodium salt. A pre-study elevation of sGGT due to alcohol consumption worsened during the course of the study. The hemoglobin concentration increased from 10.0 to 11.1 g/l whereas the PSA decreased from 725 to 3.67 ng/ml.

The Evaluation/Judgement of Clinical Response/Progression for Both Dose Levels was that of a Partial Response to the Arsenous Acid Sodium Salt.

6.3 CONCLUSION

Overall those patients taking part in dose levels 1, 3 and 5 showed, for the most part, a reduction in their PSA levels and tumour size. Most patients showed at least a partial response to the arsenous acid sodium salt with one patient showing a stable disease status. The patient in dose levels 2 and 4, H-W. S., showed a very clear response to the arsenous acid sodium salt treatment with PSA levels decreasing dramatically (99.15% reduction in tumour activity) as well as a considerable decrease in tumour size. The safety (laboratory) parameters showed no clinically significant results. The arsenous acid sodium salt was surprisingly very well tolerated with no AE's or SAE'S occurring. Overall the oral arsenous acid sodium salt, even at low doses and for relatively short treatment periods, showed a surprisingly very positive response for the treatment of prostate and/or urogenital cancer and bone metastasis.

What is claimed:

1. A method of treating multiple myeloma in a patient comprising administering a composition comprising a therapeutically effective amount of sodium meta arsenite to the patient, wherein the sodium meta arsenite composition is administered orally.

2. The method of claim 1, wherein the therapeutically effective amount is from 2.5 to 15 mg.

3. The method of claim 1 further comprising administering radiation therapy to the patient.

4. The method of claim 1 further comprising administering a chemotherapy agent to the patient.

* * * * *